United States Patent
Rall et al.

(10) Patent No.: US 7,016,716 B2
(45) Date of Patent: Mar. 21, 2006

(54) SENSOR DEVICE FOR MEASURING VITAL PARAMETERS OF A FETUS DURING BIRTH

(76) Inventors: Gerhard Rall, Bozzarisstrasse 39f, 81545 Munich (DE); Reinhold Knitza, Bergstrasse 3, 82131 Gauting (DE)

( * ) Notice: Subject to any disclaimer, the term of this patent is extended or adjusted under 35 U.S.C. 154(b) by 0 days.

(21) Appl. No.: 10/484,268

(22) PCT Filed: Jun. 28, 2002

(86) PCT No.: PCT/EP02/07178

§ 371 (c)(1),
(2), (4) Date: Aug. 18, 2004

(87) PCT Pub. No.: WO03/009747

PCT Pub. Date: Feb. 6, 2003

(65) Prior Publication Data

US 2005/0033130 A1 Feb. 10, 2005

(30) Foreign Application Priority Data

Jul. 20, 2001 (DE) .......................... 201 12 098 U

(51) Int. Cl.
*A61B 5/00* (2006.01)
(52) U.S. Cl. .................. 600/338; 600/313; 600/344
(58) Field of Classification Search ............... 600/310, 600/313, 322, 323, 338, 340, 344
See application file for complete search history.

(56) References Cited

U.S. PATENT DOCUMENTS

| | | | |
|---|---|---|---|
| 4,281,659 A | 8/1981 | Farrar et al. | |
| 4,644,957 A | 2/1987 | Ricciardelli et al. | |
| 4,658,825 A * | 4/1987 | Hochberg et al. | 600/313 |
| 5,012,811 A | 5/1991 | Malis et al. | |
| 5,154,175 A * | 10/1992 | Gunther | 600/338 |
| 5,199,432 A | 4/1993 | Quedens et al. | |
| 5,373,843 A | 12/1994 | Quedens et al. | |
| 5,411,024 A * | 5/1995 | Thomas et al. | 600/338 |
| 5,529,064 A * | 6/1996 | Rall et al. | 600/338 |
| 5,865,737 A * | 2/1999 | Rall et al. | 600/338 |
| 5,911,690 A * | 6/1999 | Rall | 600/338 |
| 6,058,321 A | 5/2000 | Swayze et al. | |

FOREIGN PATENT DOCUMENTS

EP 0611548 A 8/1994

* cited by examiner

Primary Examiner—Eric F. Winakur
(74) Attorney, Agent, or Firm—Buchanan Ingersoll PC

(57) ABSTRACT

The invention relates to a sensor device as part of a measurement appliance with a measurement device for the measurement of vital parameters of a foetus during labor and delivery, in particular the oxygen content of the blood of the foetus. Such sensor devices should be applied to the tissue of the foetus in a secure and light-tight manner, and furthermore at least the carrier or sensor should be able to be fitted to the foetus gently and easily. According to the invention, the sensor device comprises a shell-type carrier, which is subdivided into an approximately centrally arranged attachment zone and a surrounding zone, which can be brought into contact with the tissue of the foetus, and the attachment zone is provided with a spiral-type attachment element for attaching the carrier to the leading part of the foetus, and the rotational axis of the attachment element is arranged approximately perpendicular to the surface of the carrier to be fitted to the leading part of the foetus. The surrounding zone comprises at least one light emitter and at least one receiver, whereby the attachment element is supported for rotation with respect to the surrounding zone.

10 Claims, 2 Drawing Sheets

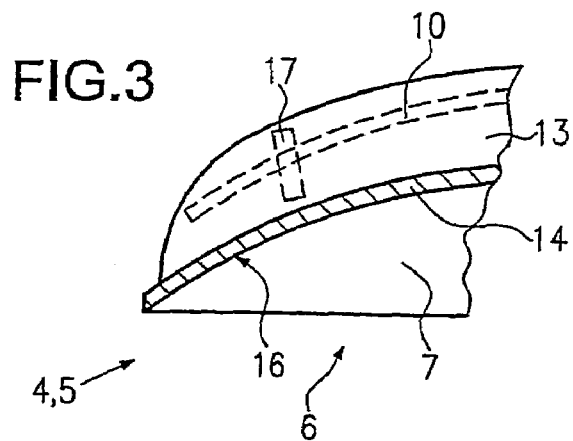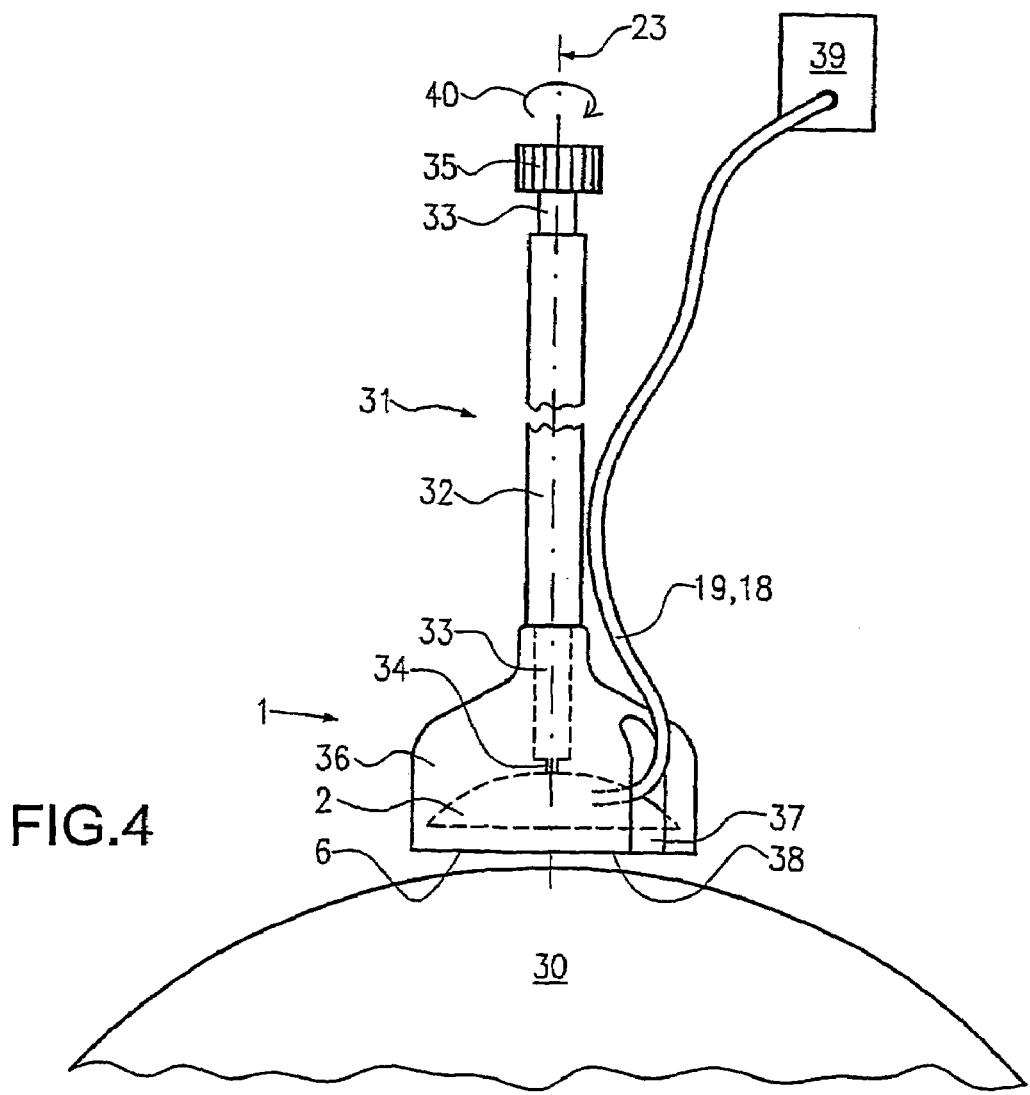

SENSOR DEVICE FOR MEASURING VITAL PARAMETERS OF A FETUS DURING BIRTH

FIELD OF THE INVENTION

The invention relates to a sensor device as part of a measurement appliance with a measurement device for the measurement of vital parameters of a foetus during labor and delivery, in particular of the oxygen content of the blood of the foetus.

BACKGROUND OF THE INVENTION

This kind of sensor device known from EP 611 548 A1 exhibits a round shell-type carrier in which an approximately central attachment zone is provided which is fitted with a spiral-type attachment element for attaching the carrier to the leading part of the foetus. Here, the rotational axis of the attachment element is approximately perpendicular to the surface of the carrier which is to be attached to the leading part of the foetus. The carrier also exhibits a marginal zone which can be brought into contact with the tissue of the foetus, the said marginal zone exhibiting a light emitter and a receiver. The marginal zone is formed as a spring element, whereby it presses flexibly onto the tissue of the foetus under the stressing of the spring. This ensures a reliable transmission of light from the emitter through the tissue of the foetus to the receiver, whereby good signals are obtained for evaluation.

For fitting the sensor device to the tissue of the foetus, the carrier is pressed against the tissue of the foetus and the sensor device rotated about the axis and in the rotational direction of the wire spiral, so that it screws into the galea of the foetus. The screwed-in wire spiral provides the counterpoint for the spring force with which the marginal zone presses onto the tissue of the foetus.

From U.S. Pat. No. 5,199,432 and U.S. Pat. No. 5,373,843 it is known that a cylindrical CTG sensor (cardiotocography) is provided at its front end with a wire spiral and is fastened by the wire spiral penetrating into the tissue of a person. For fitting, the cylindrical sensor is joined at its rear end to a rotating bar which is supported for rotation in a tube. The leads leaving the sensor extend longitudinally through the hollow space of the rotating bar and are brought out at the back.

When feeding in the sensor, the sensor is first arranged withdrawn inside the tube. Once the tube is placed on the human tissue, the sensor is pushed axially towards the front with the aid of the rotating bar and then twisted. The problem arises in that the handling of the leads running through the rotating bar and the tube is cumbersome in practice, in particular when the sensor is fitted to the tissue and the rotating bar and the tube are withdrawn when they are no longer required.

An analogous method of attachment with a wire spiral is suggested in U.S. Pat. No. 4,644,957 with which the same problems arise. With these sort of arrangements there is also the disadvantage that the tubes are often filled with amniotic fluid which contaminates the leads and plug contacts. Due to the electrolyte content of the amniotic fluid, an electrically conductive film remains which can negatively affect the sensor signals.

U.S. Pat. No. 6,058,321 describes a measurement appliance for the continuous monitoring of a foetal electrocardiogram and for the intermittent monitoring of a blood pH value of the foetal scalp during a delivery. A spiral-shaped needle for screwing into the scalp protrudes from a flat bottom of the appliance. A hollow needle of the pH probe is stored withdrawn within the appliance during the screw-in process, so that it has no contact with the tissue of the foetus. A rotatable retention ring with a receiving recess for the hollow needle of the pH probe is arranged around the base element, the said retention ring being locked onto the base element when the spiral needle is screwed in. When the spiral needle is securely attached in the scalp of the foetus, the pH probe with the retention ring can be screwed in at various spaced measurement positions from which the hollow needle of the pH probe can be extended to extract a blood sample from the foetal scalp.

SUMMARY OF THE INVENTION

The object of the invention is to develop the known sensor device of the type mentioned at the beginning, such that the existing advantages such as the secure attachment and light sealing on the tissue of the foetus are retained and furthermore, at least the carrier (sensor) can be applied to the foetus more gently and easily.

For the solution of this object the invention provides a sensor device as part of a measurement appliance with a measurement device for the measurement of vital parameters of a foetus during labor and delivery, in particular the oxygen content of the blood of the foetus, whereby the sensor device comprises a shell-type carrier which is subdivided into an approximately centrally arranged attachment zone and a surrounding zone which can be brought into contact with the tissue of the foetus, and the attachment zone with a spiral-type attachment element is provided for attaching the carrier to the leading part of the foetus, whereby the rotational axis of the attachment element is arranged approximately perpendicular to the surface of the carrier to be applied to the leading part of the foetus, and the surrounding zone comprises at least one light emitter and at least one receiver, whereby the attachment element is supported for rotation with respect to the surrounding zone.

Due to the shell-type formation of the carrier, the surrounding zone is already positioned on the tissue of the foetus during the attachment of the spiral-type attachment element and it retains its position also when the attachment element is screwed into the tissue of the foetus. The measures according to the invention ensure that when fitting the carrier to the tissue of the foetus the already contacting parts of the carrier do not need to be also rotated with the attachment element when overcoming the frictional force, i.e. the application of the carrier occurs significantly more sensitively and with more protection of the tissue.

This handling of the carrier is simplified still further if the attachment zone exhibits a rotational body to which the attachment element is mounted. Here it is of advantage if the leads transferring signals to the measurement device from the surrounding zone are arranged branched. Then the leads cannot be of hindrance when the attachment element is screwed in.

According to a preferred embodiment, the carrier can be releasably joined to a rotary handle for passing and fitting the sensor device to the leading part of the foetus and the carrier leads can be arranged branching outwards from the front end section of the rotary handle. This means that the leads can be brought out already from the front end of the rotary handle and routed further as is most practicable for the user. In particular the leads are therefore freed from the largest part of the rotary handle and are less affected by the rotary movement.

According to a particular embodiment of the invention, the rotary handle can exhibit a protective bell for accommodating the carrier and the bell wall can exhibit an opening through which leads are brought out. The carrier can be arranged in the protective bell when the sensor is passed and applied, so maternal tissue is held at a distance and protected from the carrier. This facilitates trouble-free fitting of the carrier on the tissue. Leads are brought out through the opening in the bell wall and they can be then routed as required by the user.

It is suggested that the opening for bringing out the leads opens into the funnel opening of the protective bell facing the leading part of the foetus. When releasing the rotary handle from the carrier applied to the foetus, the leads are released from the protective bell via the mouth of the opening in the bell wall towards the funnel opening and can be arranged depending on the application.

According to a special embodiment of the invention, the rotary handle may comprise a rotating bar which can be joined to the attachment zone, the rotating bar being supported for rotation in a tube-type sleeve, whereby the leads run outside of the tube-type sleeve. Whereas in the state of the art the leads ran within the sleeve and the rotating bar and with the rotation of the rotating bar an undesirable twisting of the leads with even binding of the leads or the rotating bar in the sleeve could occur, with this special embodiment of the invention undisturbed rotation of the rotating bar in the sleeve is possible. The leads can be routed outside of the sleeve. For example, it is conceivable that they are connected or clipped on outside of the sleeve, whereby this connection can also be released again where necessary.

In a particular manner the attachment element can be in electrically conducting contact with a slip-ring contact of the surrounding zone. This facilitates the use of the attachment element as an electrode despite its rotation with respect to the surrounding zone, the said electrode deriving its electrical potential via the slip-ring contact to the surrounding zone, from where it is passed on via leads. In this way for example, a wire spiral can be used as a CTG electrode.

In a particular manner the attachment zone can be supported for rotation and axially fixed via an annular shoulder held in an annular groove on the carrier. This ensures good rotating properties of the attachment zone on the carrier, whereby pressure forces in the direction of the rotational axis are also transferred to the carrier. This is particularly favourable with sensors whose surrounding zone presses on the tissue of the foetus under the stress of a spring in order to establish a good light transferring contact to the tissue of the foetus.

Particularly advantageously, the attachment zone can be latched axially on the carrier. The initially separate attachment zone can be mounted on the carrier via the latch connection, whereby the latch connection is strong enough for the forces to be transferred between the attachment zone and the carrier.

BRIEF DESCRIPTION OF THE DRAWINGS

An embodiment of the invention is illustrated in the drawing and is explained in the following. The following are illustrated.

DETAILED DESCRIPTION OF THE INVENTION

Figure 1:
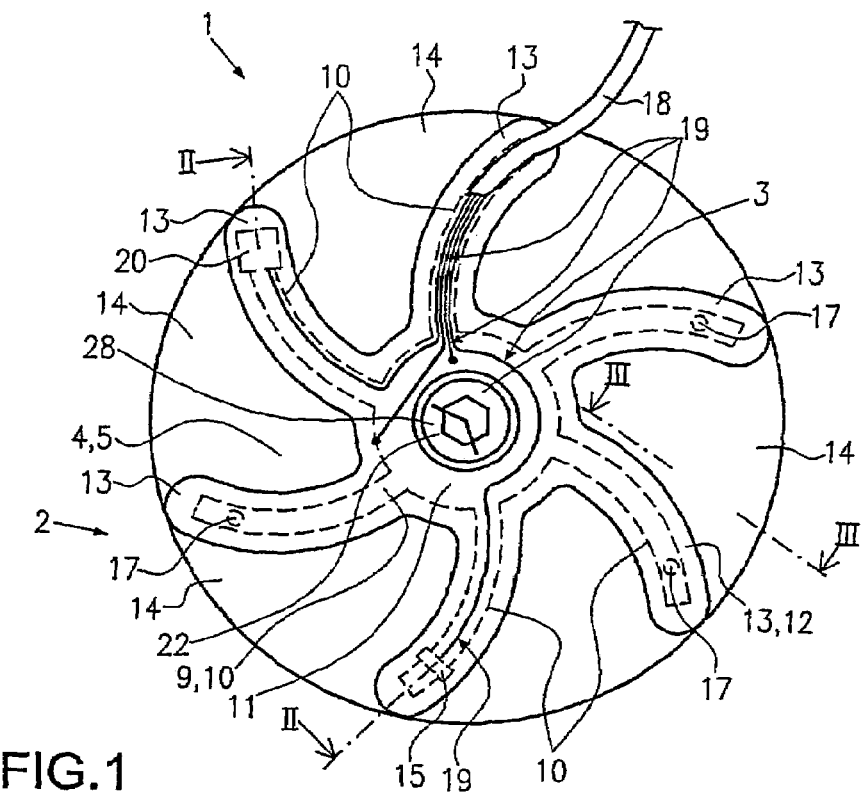
FIG. 1 a straight top view of a sensor device according to the invention.
Figure 2:
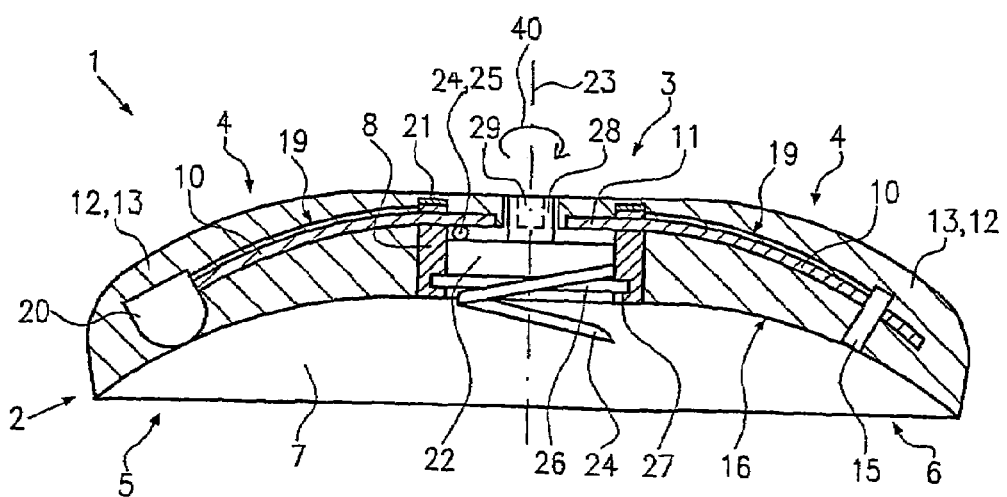
FIG. 2 a vertical cross-section through the sensor device according to the invention from FIG. 1 along the line II—II in FIG. 1, FIG. 3 a partial cross-section through the sensor device according to the invention according to FIG. 1 along the line III—III in FIG. 1, and FIG. 4 a side view of a sensor device according to the invention as part of a measurement appliance with a measurement device in a situation shortly before application to the leading part of a foetus.

In FIGS. 1 and 2 a sensor device according to the invention for the measurement of vital parameters of a foetus during birth is illustrated. Such sensor devices are also designated as pulse oxymetric sensors.

The sensor device has a carrier 2, shown approximately round in the top view, the said carrier being subdivided into an attachment zone 3 and an elastic surrounding zone 4. The attachment zone 3 is arranged approximately centrally in the carrier, whereas the surrounding zone 4 is formed as a marginal zone and surrounds the attachment zone 3.

The carrier 2 is formed as a round shell 5, curved in cross-section. On its concave side 6 facing the leading part of a foetus, it exhibits a recess 7.

The surrounding zone 4 has an approximately centrally arranged carrier ring 8, which consists of hard plastic. In the carrier ring 8 a spring star is cast which exhibits six spring arms 10 spaced radially outwards and distributed over the carrier. The spring arms 10, as seen in the top view, are curved slightly in the clockwise direction. They are formed in one piece with a central cup-spring ring 11 of the spring star 9. The spring star 9 consists of an approximately leaf shaped spring metal.

The spring star 9 is embedded in a soft silicone material which forms a shell cover 12 of the surrounding zone and forms approximately the round shape of the carrier 2. The silicone material has a hardness of about 5 Shore.

The spring arms 10 are embedded in relatively thick shell arms 13 of the shell cover 12 which enclose the spring arms 10 over their entire length.

Between the shell arms 13, the shell cover 12 is formed as a relatively thin shell skin 14 with a significantly thinner wall thickness. In FIG. 3 the thin shell skin 14, generally with a thickness of less than 1 mm, and compared to that the many times thicker shell arm 13, are illustrated schematically in a cross-sectional view with one of the spring arms 10 being embedded in the shell arm 13.

A light emitter 15, which is fitted approximately at the end section of one of the spring arms 10, is positioned flush with the locating face 16 facing the foetus. At the end of another spring arm 10 a light receiver 20 is arranged which is also flush with the locating face 16.

Three other spring arms 10 bear, near their end section, a reinforcing rib 17 of hard plastic arranged approximately perpendicular to their direction of extension, the said reinforcing rib being fully enclosed by material of the shell arm 13, as illustrated in FIG. 3.

On one of the spring arms 10 a cable is routed from the outside which extends into the corresponding shell arm 13 and is attached to the spring arm 10. The cable 18 extends approximately in a slightly tangential direction of the end of the spring arm. A number of leads 19 of the cable 18 extend within the shell cover 12. One lead each goes to the emitter 15 and the receiver 20, whereby these two leads are each formed with two cores.

One of the leads 19 extends to the cup-spring ring 11 and another lead 19 extends to a metal contact element 21, which is fitted to the carrier ring 8. Signals for the cardiotocography can be obtained through the leads to the contact element 21 and the cup-spring ring 11.

The attachment zone 3 exhibits a rotational body 22 of hard plastic which is supported for rotation within the carrier ring 8. The rotational axis 23 runs perpendicular to the locating face 16 in the region of the rotational body 22. The direction of rotation is indicated by the arrow 40.

A wire spiral 24, which protrudes at the side 6 from the rotational body 22 with not quite one winding, is embedded in the rotational body 22. At the side 6 the rotational body meets the locating face 16 approximately flush.

The wire spiral can, for example, also be cast by injection moulding during the manufacture of the rotational body 22. One end of the coil 25 of the wire spiral 24 is in conducting contact with the cup-spring ring 11, so that a slip-ring contact is formed with the wire spiral 24 on rotational the rotational body 22.

The rotational body 22 exhibits circumferentially a radially spaced annular shoulder 26, which engages an annular groove 27 formed on the inner side of the carrier ring 8 and can be rotated in it. This means that the rotational body 22 is supported for rotation, but is fixed axially.

For mounting the rotational body 22 in the carrier ring 8, the annular shoulder 26 can be latched into the annular groove 27. Alternatively it is conceivable that the annular shoulder is designed open on one side in the axial direction and after inserting the rotational body 22 a groove wall is placed on the open end and, for example, ultrasonically welded to the carrier ring 8. Alternatively, the rotational body 22 can be formed with the wire spiral 24 as a disposable element, which can be replaced by another one after use.

On the side turned away from side 6 the rotating shoulder has a tapered section 28 in which an internal hexagon is formed centrally. The tapered section 28 extends through the shell cover 12 and is accessible from outside.

In FIG. 4 the situation when fitting a sensor device on the leading part of a foetus is illustrated, whereby the head 30 of the foetus is indicated as an example. The carrier 2 is fitted to a rotary handle 31. It exhibits an outer tube 32, which can be bent to a limit and through which a rotating bar 33, which can also be bent to a limit, extends. At its end facing the head 30, the rotating bar 33 exhibits a hexagon 34 which engages the internal hexagon 29. At the side facing away from the foetus, the rotating bar 33 protrudes out of the tube 32 and has at its end a rotating collar 35 which can be manually turned by a person. The rotating bar 33 can be moved axially in the tube 32.

At the end of the tube 32 facing the foetus a protective bell 36 is attached in which the carrier 2 is accommodated. The cable 18 of the carrier 2 branches in the front region of the rotary handle 31 through a slotted opening 37 in the wall of the protective bell 36 and therefore passes to the outside. The opening 37 runs into the funnel opening 38 of the protective bell 36 facing the foetus. The cable passing outwards through the opening 37 runs outside of the tube and is connected to a measurement device 39 which evaluates the signals obtained.

In the following the application and functioning principle of the embodiment of a sensor device according to the invention and illustrated in the drawing is explained in more detail.

Starting from the situation illustrated in FIG. 4, a person operates the rotary handle 31 and therefore moves the sensor device 1 with the carrier 2 inside the protective bell 36 towards the head 30 of the foetus. The protective bell 36 is placed on the head 30 and the rotary bar 33 is pushed to the front axially, so that the carrier 2 is pressed onto the head. Here, the surrounding zone 4, which is more curved than the statistically average curvature of the head of the foetus, is pressed on such that it lies on the head under spring stressing and acts as a spring means. The light emitter 15 and the receiver 20 are pressed adjacently against the head 30.

In the depressed state, the rotating bar 33 is turned in the direction of the coil of the wire spiral 24 so that it screws into the galea of the foetus. When this occurs, only the rotational body 22 with the wire spiral 24 turns. The surrounding zone 4 remains unturned in firm contact on the head of the foetus. The cable 18 branching from the surrounding zone 4 is not affected by the rotation and extends radially outwards through the opening 37.

After the wire spiral 24 has been firmly turned, the rotary bar 33 is withdrawn, whereby it is released from the carrier 2. Here, the tube with the protective bell can also be withdrawn, so that only the carrier 2 remains on the head. The lead can be brought out from the protective bell 36 through the connection of the opening 37 with the funnel opening 38. The carrier fitted to the head retains its spring contact with the head of the foetus through the prestressed spring arms 10 of the surrounding zone 4 and only the cable 18 branches off to the measurement device 39.

The invention claimed is:

1. Sensor device as part of a measurement appliance with a measurement device for the measurement of vital parameters of a foetus during labor and delivery, including the oxygen content of the blood of the foetus, wherein the sensor device comprises a shell-type carrier, which is subdivided into an approximately centrally arranged attachment zone and a surrounding zone, which can be brought into contact with the tissue of the foetus, and the attachment zone is provided with a spiral-type attachment element for attaching the carrier to the leading part of the foetus, wherein the axis of rotation of the attachment element is arranged approximately perpendicular to the surface of the carrier to be fitted to the leading part of the foetus, and the surrounding zone comprises at least one light emitter and at least one receiver, and wherein the attachment element is supported for rotation with respect to the surrounding zone.

2. Sensor device according to claim 1,
wherein
the attachment zone comprises a rotational body to which the attachment element is attached.

3. Sensor device according to claim 1,
wherein
the leads transferring the signal to the measurement device are arranged branching off from the surrounding zone.

4. Sensor device according to claim 1,
wherein a rotary handle is provided, whereby
the carrier can be releasably connected to the rotary handle for moving and fitting the sensor device to the leading part of the foetus and leads of the carrier are arranged branching off towards the outside from the front end section of the rotary handle.

5. Sensor device according to claim 4,
wherein
the rotary handle exhibits a protective bell for accommodating the carrier and the bell wall exhibits an opening through which the leads are brought out.

6. Sensor device according to claim 5,
wherein
the opening for routing the leads runs into the funnel opening of the protective bell facing the leading part of the foetus.

7. Sensor device according to claim 4,
wherein
the rotary handle exhibits a rotating bar which can be connected to the attachment zone, said rotating bar being mounted for rotation in a tube-type sleeve, whereby the leads run outside of the tube-type sleeve.

8. Sensor device according to claim 1,
wherein
the attachment element is in electrically conducting contact with a slip-ring contact of the surrounding zone.

9. Sensor device according to claim 1,
wherein
the attachment zone is supported on the carrier for rotation via an annular shoulder supported in an annular groove and is axially fixed.

10. Sensor device according to claim 1,
wherein
the attachment zone is latched axially on the carrier.

* * * * *